US009795772B2

United States Patent
Aggerholm et al.

(10) Patent No.: US 9,795,772 B2
(45) Date of Patent: Oct. 24, 2017

(54) ENDOLUMINAL DRUG DELIVERY DEVICE

(71) Applicant: COOK MEDICAL TECHNOLOGIES LLC, Bloomington, IN (US)

(72) Inventors: Steen Aggerholm, Heddinge (DK); Christina Rauff Hansen, Koebenhavn (DK); Sean D. Chambers, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 202 days.

(21) Appl. No.: 14/724,047

(22) Filed: May 28, 2015

(65) Prior Publication Data

US 2016/0045341 A1    Feb. 18, 2016

(30) Foreign Application Priority Data

Aug. 15, 2014   (GB) .................................. 1414547.8

(51) Int. Cl.
*A61F 2/06* (2013.01)
*A61M 31/00* (2006.01)
*A61M 25/10* (2013.01)

(52) U.S. Cl.
CPC ..... *A61M 31/00* (2013.01); *A61F 2230/0067* (2013.01); *A61F 2230/0069* (2013.01);
(Continued)

(58) Field of Classification Search
CPC .. A61F 2/90; A61F 2/844; A61F 2/958; A61F 2/06; A61M 25/104; A61M 25/1029; A61M 31/00; A61M 29/00
See application file for complete search history.

(56) References Cited

U.S. PATENT DOCUMENTS

| 7,641,844 B2 | 1/2010 | Melsheimer |
| 8,226,603 B2 | 7/2012 | Von Oepen et al. |

(Continued)

FOREIGN PATENT DOCUMENTS

| EP | 0518704 | 12/1992 |
| EP | 2732798 | 5/2014 |
| WO | WO2012/097287 | 7/2012 |

OTHER PUBLICATIONS

Combined Search and Examination Report for GB1414547.8 dated Feb. 13, 2015, 7 pgs.

(Continued)

*Primary Examiner* — Victor Nguyen
(74) *Attorney, Agent, or Firm* — Brinks Gilson & Lione

(57) ABSTRACT

A drug delivery device (10) includes expandable element (12) formed of a braided structure having a body portion (16) and first and second end cones (18, 20). The end cones are attached at their necks (22, 24) to a catheter assembly (14). The expandable element (12) can expand to a vessel contacting configuration, in which the body portion (16) contacts the vessel wall. Bioactive agent (28) covers at least the outer surface of the body portion (16) such that bioactive material can be administered to a vessel wall. The end cones (18, 20) have an open structure allowing unrestricted passage of blood through the device (10) in the deployed configuration, such that blood flow can be maintained during the administration of bioactive agent (28) from the device (10). The expandable element (12) can be radially contracted by extending it in the longitudinal direction, both for deployment endoluminally to the treatment site and also for retrieval following the administration of the bioactive material.

16 Claims, 4 Drawing Sheets

(52) U.S. Cl.
CPC ............ *A61F 2250/0065* (2013.01); *A61F 2250/0067* (2013.01); *A61M 2025/105* (2013.01); *A61M 2025/1081* (2013.01)

(56) References Cited

U.S. PATENT DOCUMENTS

| | | |
|---|---|---|
| 2001/0035456 A1 | 11/2001 | Lennox |
| 2002/0010418 A1 | 1/2002 | Lary et al. |
| 2002/0090388 A1 | 7/2002 | Humes et al. |
| 2006/0259005 A1 | 11/2006 | Konstanino et al. |
| 2007/0207179 A1 | 9/2007 | Andersen et al. |
| 2013/0287003 A1* | 10/2013 | Kim ............... H04J 11/0093 370/331 |

OTHER PUBLICATIONS

Preliminary Examiner Report for GB1414547.8 dated Feb. 16, 2015, 2 pgs.

* cited by examiner

ENDOLUMINAL DRUG DELIVERY DEVICE

RELATED APPLICATION

The present patent application claims the benefit of the filing date of GB Patent Application Number 1414547.8, filed Aug. 15, 2014, the contents of which is hereby incorporated by reference.

TECHNICAL FIELD

The present invention relates to an endoluminal drug delivery device for delivering bioactive agents to a vessel wall.

BACKGROUND

Various technologies have been developed to deliver bioactive agents to a vessel wall for treating a variety of medical indications. One example involves the application of an anti-restenosis agent to a vessel wall following or sometimes during an angioplasty procedure. Another example is in the localised treatment of tumours.

One technology involves the use of a drug coated medical balloon, which is inflated against the vessel wall in order to bring the bioactive agent into contact with the vessel tissue for transfer of the bioactive agent into the affected tissue. This may be by way of elution from the balloon, by injection through apertures or pores in the balloon, from simple transfer of the bioactive agent from the balloon surface, and so on. It is also known to use one or more medical balloons to stop blood flow in the vessel, which in effect closes off the vessel, and then to inject bioactive agent into the vessel or otherwise administer bioactive agent into the vessel while the vessel is blocked.

A problem with such medical balloons is that they choke off blood supply from organs downstream of the balloon, and as a result any procedure involving such balloons is time limited.

Attempts have been made to overcome the limitations of such balloons, by developing balloons having an internal lumen which allows continued passage of blood through the balloon. Such balloons could be described as having an elongate doughnut shape. These balloons, however, have a significant deflated volume, which reduces their compressibility and flexibility, leading to challenges in their endoluminal delivery to the treatment site. It also makes such balloons unsuitable for treating small diameter vessels including the cerebral vessels. The lumen through the balloon is also necessarily restricted, leading to reduced blood flow in the vessel.

It is also known to have drug coated stents which are implanted into the vessel. While stents will not generally impinge on the flow of blood through the vessel, they result in a foreign object being left in the patient, either permanently or until the stent is removed during a second medical procedure.

Some examples of devices for administering drugs into a vessel of a patient are disclosed in U.S. Pat. Nos. 7,641,844, 8,226,603, US-2001/0035456, US-2007/0207179, US-2002/0090388 and US-2002/0010418, the contents of which are incorporated by reference.

DISCLOSURE

The present invention provides an improved endoluminal drug delivery device for delivering one or more bioactive agents into a vessel of a patient.

According to an aspect of the present invention, there is provided a delivery device for delivering a bioactive agent to a vessel wall, including: an expandable frame element having a body portion and first and second end portions, the body portion being radially expandable from a contracted to a deployed configuration, and having an open interior and an outer surface; the first and second end portions having an open structure allowing passage to the open interior of the body portion; a carrier element on which the expandable frame is disposed, wherein the first and second end portions are connected to the carrier element; and a bioactive material disposed at least on the outer surface of the body portion.

The device can be of a type which is deployed in a patient solely for the duration of the drug delivery phase and is of a structure that blood can continue to flow through the vessel during the procedure. The expandable portion of the device remains affixed to the carrier element and can therefore be withdrawn from the patient's vasculature without having to undergo a second medical intervention.

Preferably, the body portion is generally hollow; which optimises the compressibility of the device and therefore can minimise its contracted or collapsed footprint.

The body portion may be generally cylindrical, therefore being able to abut the inner surface of a vessel for optimum drug delivery.

In one embodiment, at least the body portion is formed of at least one braided or knitted wire.

The first and second end portions may have a tapering configuration in the deployed condition of the body portion and include a narrow end connected to the carrier element and a wide end connected to the body portion. The first and second end portions preferably have generally conical shapes when the body portion is in its deployed configuration.

Advantageously, the first and second end portions are formed of at least one braided or knitted wire.

In the preferred embodiment, the body portion has, in the expanded condition, a knit or braid weave which is tighter or denser than a knit or braid weave of the end portions.

The expandable frame element is most preferably self-supporting at least in the expanded configuration.

In an embodiment, the carrier element includes first and second carrier members, each attached to a respective one of the first and second end portions, the first and second carrier members being movable towards and away from one another, said movement causing radial expansion and contraction of the body member. In this embodiment, the structure is preferably such that movement of the carrier members towards one another causes longitudinal contraction of the expandable frame element and radial expansion of the body member, whereas movement of the carrier members away one another causes longitudinal expansion of the expandable frame element and radial contraction of the body member. In these embodiments, the first and second carrier members are preferably telescopic elements.

There may be provided an expansion device disposed within the expandable frame element. The expansion device may be an inflatable balloon, which is preferably inflatable to expand the frame element and wherein the frame element remains in the expanded configuration on subsequent deflation of the balloon.

Other features and advantages will become apparent form the description which follows and in the accompanying drawings.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
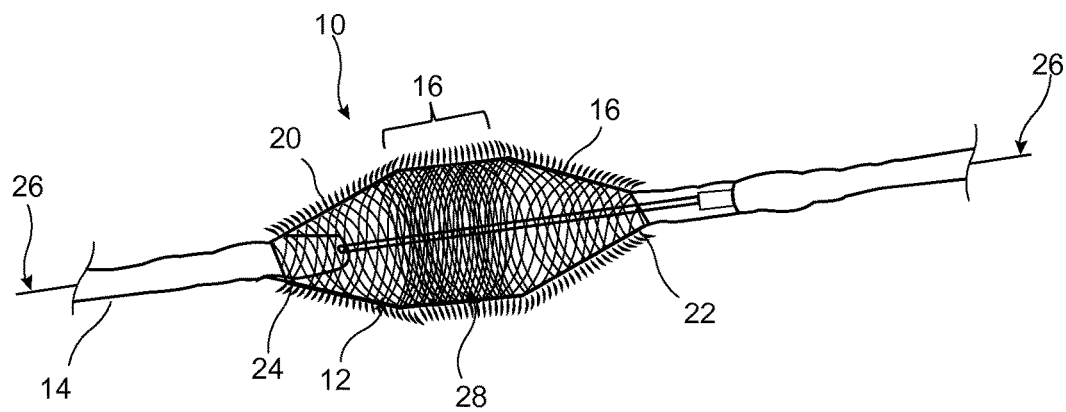
FIG. 1 shows a side elevational view of an embodiment of endoluminal drug delivery device.

The accompanying drawings are schematic only. It is to be understood that the dimensions and proportions of the various components of the devices shown in the drawings are not to scale or in proportion relative to one another. It is also to be understood that the drawings depict only the principal components of the device shown therein and that other elements and components of the device which are not central to understanding the teachings herein have been omitted for the sake of clarity.

The preferred embodiments described below are directed to an endoluminal drug delivery device having one or more expandable elements formed of braided or knitted wire. However, as described below, it is not necessary for the device to have a braided form as alternative structures are possible, with some of these being described below.

Referring first to FIG. 1, this shows an embodiment of drug delivery device 10 which has a single expandable element 12 mounted to a catheter assembly 14. The catheter assembly 14 has a distal end to which the expandable element 12 is attached and a proximal end (not visible in FIG. 1) which is generally kept outside the patient during the medical procedure and used in the deployment of the device 10, as well as in retrieving the device 10 at the end of the procedure.

The expandable element 12 is in this example formed of a braided wire and includes three zones 16, 18 and 20. The zone 16 is the central zone of the expandable element 12 and can be described as being the body portion of the element. The portions 18 and 20 are end portions and in this example are substantially conical when the device 10 is in the deployed configuration shown in FIG. 1. Each end zone 18, 20 includes a wide end coupled to the body portion 16 and having a diameter substantially the same as the diameter of the body portion 16, as well as a narrow end having a diameter substantially the same as the outer diameter of the catheter assembly 14. In practice, the narrow ends or necks 22, 24 of the end cones 18, 20 are attached to a part of the catheter assembly 14, again in a manner which will be described below.

In the embodiment shown in FIG. 1, the entirety of the expandable element 12 is made of a wire braid, either a single filament or of multifilament form. The braiding is, in the deployed state, less dense at the end cones 18, 20 and more dense at the body portion 16. It is preferred that the end cones 18, 20 have a braiding density which does not significantly impact upon the flow of blood through the expandable element 12. In practice the braid pitch or angle, relative to the longitudinal axis 26 of the device, of the braiding in the body portion is greater than that in the end cones 18, 20.

In the preferred embodiment, the body member 16 and the end cones 18, 20 are substantially circular in axial cross-section, that is in a direction normal to the longitudinal axis 26. In other embodiments, the expandable element could have a non-round cross-section, for example oval or polygonal. A round cross-section is, however, preferred as this more closely matches the internal shape of a blood vessel.

At least the outer surface of the body portion 16 has a coating 28 of bioactive material, this being shown schematically in FIG. 1. In some embodiments, the bioactive material 28 is disposed only over the extent of the body portion 16, whereas in other embodiments and as shown in FIG. 1, the bioactive material 28 may also extend along the end cones 18, 20. The bioactive material 28 may simply cover the wires of the braid and more specifically at least the outer surfaces thereof, although in other embodiments the bioactive material may have a sheet-like continuous form which also extends over any spaces between the wire braiding of the body portion 16, in which case the bioactive material 28 does not extend over the extent of the end cones 18, 20. For such an embodiment, the braiding may be covered with a continuous polymer such as urethane or silicone, with the bioactive agent applied over the covering.

The bioactive material may be any of the bioactive materials known for treating a plurality of known medical conditions. Just some examples of the large range of bioactive materials which can be applied to the expandable element 12 include but are not limited to: paclitaxel, heparin, azathioprine or azathioprine sodium; basiliximab; cyclosporin or cyclosporine (cyclosporin A); daclizumab (dacliximab); glatiramer or glatiramer acetate; muromonab-CD3; mycophenolate, mycophenolate mofetil (MMF), mycophenolate morpholinoethyl or mycophenolic acid; tacrolimus (FK506), anhydrous tacrolimus or tacrolimus monohydrate; sirolimus; interferon alfa-2a, recombinant (rIFN-A or IFLrA); antilymphocyte immunoglobulin (ALG), antithymocyte immunoglobulin (ATG), antilymphocyte serum, antithymocyte serum, lymphocytic antiserum or thymitic antiserum; brequinar or brequinar sodium; cyclophosphamide, cyclophosphamide monohydrate or anhydrous cyclophosphamide; dactinomycin, actinomycin C, actinomycin D or meractinomycin; daunorubicin, daunorubicin hydrochloride, daunomycin hydrochloride or rubidomycin hydrochloride; doxorubicin, doxorubicin hydrochloride, adriamycin or adriamycin hydrochloride; fluorouracil; gusperimus or gusperimus hydrochloride; inolimomab; leflunomide; mercaptopurine, mercaptopurine monohydrate, purinethiol or anhydrous mercaptopurine; methotrexate, methotrexate sodium, methotrexate disodium, alpha-methopterin or amethopterin; mustine, mustine hydrochloride, chlormethine hydrochloride, chlorethazine hydrochloride, mechlorethamine hydrochloride or nitrogen mustard (mustine); mizoribine; vinblastine, vinblastine sulfate or vincaleukoblastine sulphate; a pharmacologically or physiologically acceptable salt of any of the foregoing; or a pharmacologically or physiologically acceptable mixture of any two or more of the foregoing. These bioactive agents have effects known in the art including as thrombolytics, vasodilators, antihypertensive agents, antimicrobials or antibiotics, antimitotics, antiproliferatives, antisecretory agents, non-steroidal anti-inflammatory drugs, immunosuppressive agents, growth factors and growth factor antagonists, anti-tumor and/or chemotherapeutic agents, antipolymerases, antiviral agents, photodynamic therapy agents, antibody targeted therapy agents, prodrugs, sex hormones, free radical scavengers, antioxidants, biologic agents, radiotherapeutic agents, radiopaque agents and radiolabelled agents.

As will be apparent from FIG. 1, the body portion 16 is tightly braided and in practice preferably has very few of interstices between the wires of the braid. On the other hand, the end cones 18, 20 have significant gaps or spaces between the wires of the braid, thus a much looser braid structure. As a result, any bioactive material 28 coating the wires of the braid of the expandable element 12 will be more concentrated within the zone of the body portion 16 compared to the zones of the end cones 18, 20.

It is not excluded that bioactive material may coat all the way round the wires of the expandable element 12, in which case bioactive material will also extend to the side of each wire as well as the internal surfaces of the wires forming the expandable member 12. Any such bioactive material will not generally come into direct contact with the vessel wall.

Typically, the bioactive material 28 could be sprayed or otherwise deposited onto the wire or braiding of the expandable element 12. In most instances, the bioactive material will attach itself to the wire braiding by natural adhesion of the bioactive material, although in other embodiments a bonding agent may be used. It is also envisaged that in some embodiments the outer surface of the wire braiding could be treated, for example by roughening, to enhance the attachment bioactive material 28 to the expandable element 12.

The body portion 26 may have a length of a few millimeters to one or more centimeters, depending upon the size of the vessel and length of the vessel desired to be treated. For example, the body portion could have a length of between 20 mm to 200 mm for most medical applications.

The wire forming the braid of the expandable element 12 may have a diameter in the range of around 0.05 mm to around 0.25 mm, preferably from around 0.1 mm to around 0.2 mm. A braid of around 0.15 mm for a 2.7 French deployed diameter device has been used effectively. The skilled person will appreciate that the diameter of the braid may vary from the indications given, with a thicker wire providing greater opening force, but at the expense of reduced compressibility and flexibility. A thinner braid wire provides a more compressible and flexible device, with lower opening force.

Figure 2:
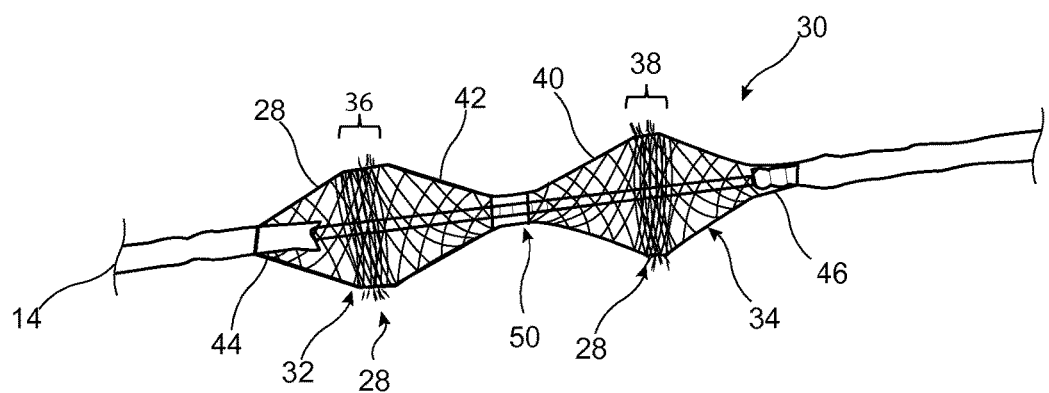
FIG. 2 shows a side elevational view of another embodiment of endoluminal drug delivery device.

Referring now to FIG. 2, this shows another embodiment of drug delivery device 30, which is very similar to the device 10 of FIG. 1, with the principal difference being that the device 30 has first and second expandable elements 32, 34 disposed adjacent one another in the longitudinal direction of the device 30.

Each expandable element 32, 34 includes a body portion 36, 38, respectively, and first and second end zones 40, 42. In this embodiment, the necks 44, 46 of the expandable element 30 are attached to respective parts of the catheter assembly 14, in a manner described in further detail below, while between the first and second expandable elements 32, 34 there is a constriction 50 in the structure 30. The constriction may be a sleeve of material which holds the wire braiding forming the expandable elements 32, 34 in a radially constrained configuration. The sleeve 50, or other constriction, is preferably slidable over the elements of catheter assembly 14, although in other embodiments may be fixed to the catheter assembly 14. The sleeve could be made of metal, for example the same material as the wire braiding.

As with the embodiment of FIG. 1, the body portion 36, 38 of the expandable element 32, 34 has a tighter wire braiding than the end cones 40, 42. As with the embodiment of FIG. 1, the end cones 41, 42 preferably are a wire braiding of which the wires are sufficiently spaced apart to provide substantially unimpeded flow of blood through the device 30 when it is in its expanded, deployed, condition as shown in FIG. 2.

In the embodiment of FIG. 2, the body portions 36, 38 are shown being shorter than the body portion 16 of the embodiment of FIG. 1. The length of the body portion(s) of the drug delivery device is preferably chosen for the particular treatment to be effected by the drug delivery device. This can vary from a few millimeters to one or more centimeters.

Figure 3:
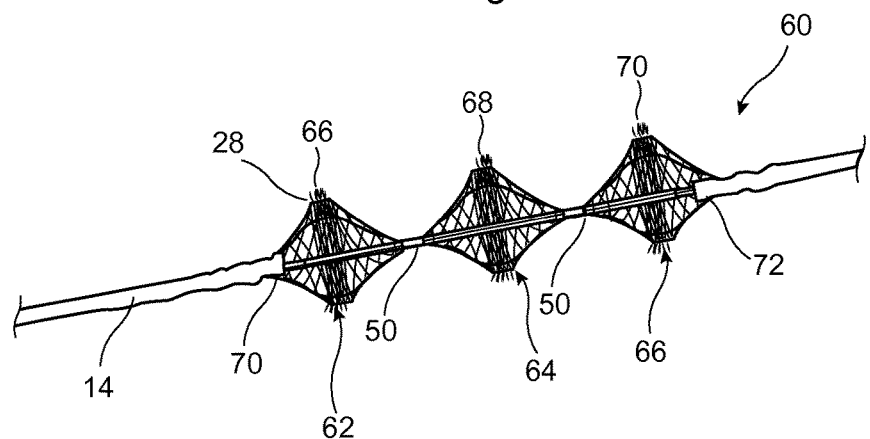
FIG. 3 shows a side elevational view of another embodiment of endoluminal drug delivery device.

Referring now to FIG. 3, this shows another embodiment of drug delivery device 60 similar to the embodiments of FIGS. 1 and 2, and which in this case includes three expandable elements 62, 64, 66 arranged lineally along the catheter assembly 14 to provide three zones of drug delivery, being the body portions 66, 68, 70 of each of the expandable elements 62-66. Each expandable element 62-66 can have the same structure and be made of the same materials as the expandable elements 10 and 22, 24 of the embodiments of FIGS. 1 and 2 and can equally be made of braided wire. As will be apparent from FIG. 3, the embodiment of drug delivery device 60 shown in this drawing includes two constriction elements or sleeves 50 for maintaining the device 60 radially constricted between the expandable elements 66-70. As with the embodiment of FIG. 2, the constricting elements 50 could be able to slide on the catheter assembly 14, although in other embodiments may be fixed to parts of the catheter assembly 14.

As the earlier described embodiments, the outer surfaces at least of the body portions 66-70 are provided with a bioactive material 28 thereon. Also, similarly to the previously described embodiments, the bioactive material 28 could extend along the end cones of each expandable elements 62-66 and could cover more or indeed all of the surfaces of the wire braiding rather than just the outside surfaces thereof.

With respect to the embodiments of FIGS. 2 and 3, it is not necessary to provide the same bioactive material 28 coating on each expandable element 32 and 34, or 62-66 as there may be provided different bioactive agents on each of the expandable elements of the device.

It is preferred, in connection with the embodiments of FIGS. 2 and 3, that the expandable elements of each drug delivery device 30, 60 are formed from a common wire braiding, although it is not excluded that the expandable elements could be individual elements connected together, for instance, by the restriction elements 50 or by any other suitable connector element.

Figure 4:
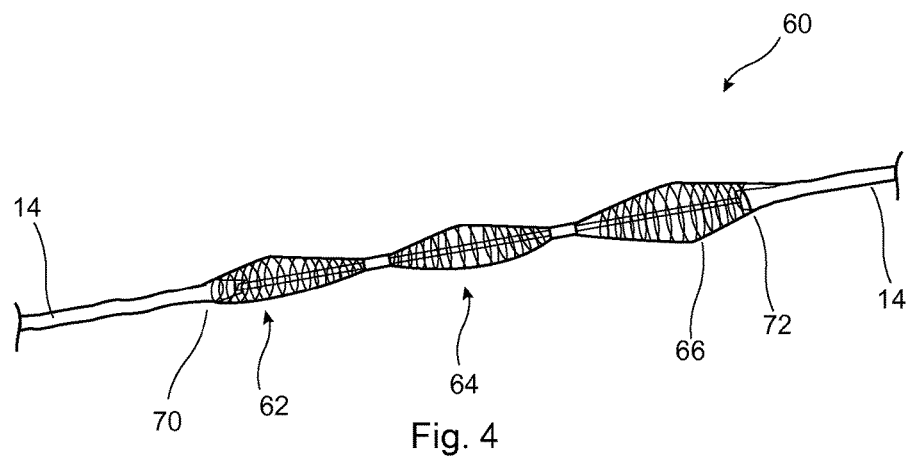
FIG. 4 shows the endoluminal drug delivery device of FIG. 3 ion a partially contracted configuration.

Referring now to FIG. 4, this shows the embodiment of drug delivery device 60 of FIG. 3 in a radially contracted configuration and specifically in which the expandable elements 62-66 are pulled longitudinally, which causes their radial contraction as will be apparent from a comparison of FIGS. 3 and 4. When the device 60 is fully elongated, the expandable elements 62-66 are preferably substantially flat, that is they preferably do not expand radially outwardly along their length and have substantially uniform outer diameters between the two ends 70, 72 of the device 60. It is not necessary for the expandable elements 62-66 to become fully flattened, although this is preferred as it minimises the diameter of the device 60 for delivery purposes and as a result the diameter of any delivery catheter used for delivering the device endoluminally through the patient's vasculature to the treatment site.

Figure 5:
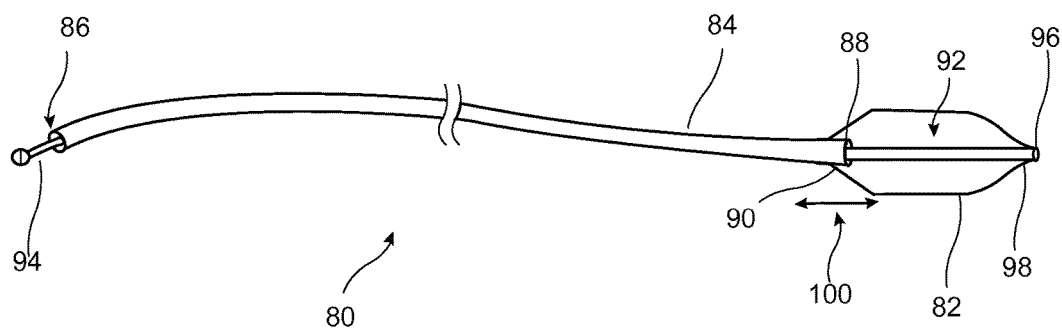
FIG. 5 is a schematic diagram showing the elements of a delivery and support catheter assembly for the devices of FIGS. 12 to 4.

Referring now to FIG. 5, this shows an embodiment of catheter assembly 80 which can be used for deploying a drug delivery device of the type depicted in FIGS. 1 to 4. FIG. 5 is a schematic diagram in which the expandable element 82 is equivalent to standard element 12 of the embodiment of FIG. 1, in outline only. It will be apparent that the expandable element 82 can be formed precisely as that in the embodiment in FIG. 1. The catheter assembly 80 has a first catheter element 84 of elongate form with a proximal end 86, which typically remains outside a patient, and a distal end 88, which is disposed within the zone of the expandable element 82 and is specifically attached to the neck 90 of the expandable element 82. The catheter assembly 80 also includes a second elongate element 92 which in the preferred embodiment is a catheter having a lumen extending therethrough, so that the catheter assembly 80 can be delivered over a guide wire, although which in other embodiments could be a wire or flexible rod. The element 92 includes a proximal end 94 and a distal end 96. The distal end 96 is attached to the end 98 of the expandable element 82.

As will be apparent from the arrow 100 in FIG. 5, the catheter elements 84, 92 are slidable relative to one another so that the distal ends 88, 96 thereof can move towards or away from one another. When the distal ends 88, 96 are brought closer together, the spacing between the ends 90, 98 of expandable element 82 is likewise reduced, causing the expandable element 82 to expand radially outwardly. By contrast, when the distal ends 88, 96 of catheter elements 84, 92 moved away from one another, this stretches the expandable element 82 by pulling the ends 90, 98 apart, thereby causing the expandable element 82 to contract radially in a manner equivalent to the view of FIG. 4.

The embodiment of FIG. 5 provides a control mechanism for controlling the expansion of the expandable element 82 using two catheter elements 84, 92 and in which the element 92 slides within an internal lumen of the catheter element 84. A person skilled in the art will be able to devise other structures which provide the same effect of moving the ends 90, 98 of expandable element 82 towards and away from one another. The precise mechanism by which this is achieved is, therefore, not critical to the teachings herein.

The embodiment of FIG. 5 has a single expandable element 82 and it will be apparent that embodiments having a plurality of expandable elements, such as the embodiments of FIGS. 2 and 3, these will be mounted onto a catheter assembly equivalent to the catheter assembly 80 shown in FIG. 5. With such embodiments, the constricting elements 50 could be disposed over the inner catheter element 92 and slidable thereon.

In connection with the embodiments of FIGS. 1 to 5, it is preferable that the expandable elements have a natural non-biased condition in which they are radially expanded, as shown in FIGS. 1 to 3. Thus, expandable elements of the drug delivery device will tend towards their wider, deployed, configuration. In such a case, the deployment mechanism will pull the expandable elements in a longitudinal direction in order to cause them to contract radially. For such a purpose, the wire braiding could be formed of a spring material such as spring steel, shape memory alloy such as Nitinol or the like. In other embodiments, the expandable elements could in their rest condition be radially contracted, in which case they will be biased against spring bias into the radially expanded configuration, by appropriate adjustment of the elements of the catheter assembly. It is not excluded, though, that the wire braiding can in some embodiments have no particular bias, with the state of the expandable elements being determined solely by the positioning of the various elements of the catheter assembly.

The braid can usefully be made of an oxide free alloy, such as Nitinol.

The wire of the braid may have a smooth outer surface although may also have a textured or roughened outer surface to enhance retention of bioactive material thereon. The wire can be roughened or textured by any known method including, for example, abrasion, etching, blasting and the like.

It is preferred in all of the embodiments of drug delivery device disclosed herein that the expandable elements are self-supporting once in the deployed condition. In other words, when the elements of the catheter assembly are positioned such that the expandable elements can and do expand radially outwardly, there is no other radially expanding device required to hold the expandable elements in their radially expanded condition. The expandable elements will therefore retain their shape by the strength and/or opening force of their structures, in the preferred embodiments or the wire braiding.

Figure 6:
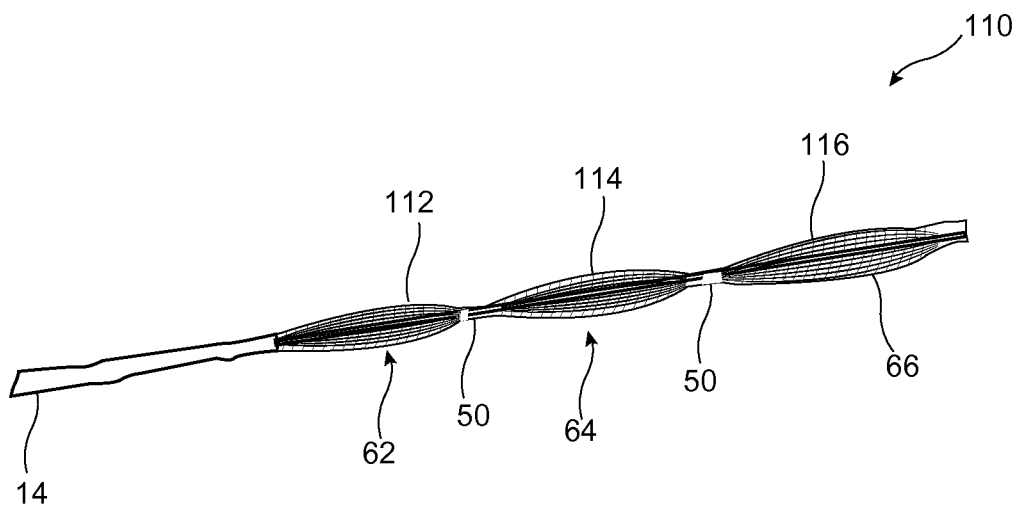
FIG. 6 is a side elevational view of another embodiment of endoluminal drug delivery device.
Figure 7:
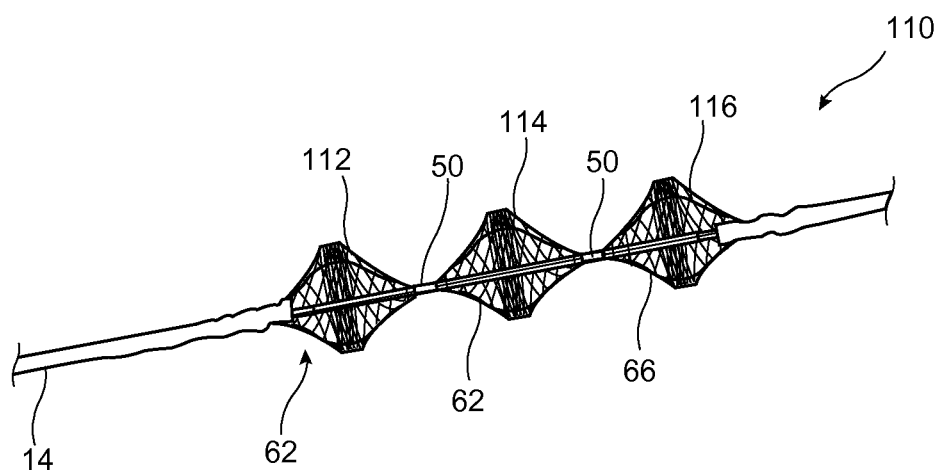
FIG. 7 is a view of the device of FIG. 6 in an expanded condition.

Referring now to FIGS. 6 and 7, these show another embodiment of drug delivery device 110 which has similarities to the embodiment shown in FIGS. 3 and 4. The drug delivery device 110 includes a catheter assembly 14 as well as first and second expandable elements 62-66 made of wire braiding as in the embodiment of FIGS. 3 and 4. The difference lies in the provision of a plurality of inflatable balloons 112, 114 and 116, each disposed within a respective expandable element 62-66. In this embodiment, the catheter assembly 14 includes at least one inflation lumen coupled to the inflatable balloons 112-116. It is not excluded that the catheter assembly may be provided with a plurality of lumens, each individually coupled to a respective one of the inflatable balloons 112-116 so that these can be inflated independently of one another.

In FIG. 6, the balloons 112-116 are shown in a deflated form and the expandable elements 62-64 in a radially collapsed configuration. By contrast, in FIG. 7 the inflatable balloons 112-116 have been inflated by a suitable inflation fluid, typically saline solution. The expandable element 62-64 can be seen having expanded and are consistent with expansion of the balloons 112-116 and into a configuration in which in practice they would be deployed against the walls of a vessel.

The provision of the inflatable balloons 112-116 in the embodiment of FIGS. 6 and 7 can in some circumstances be useful in assisting in the expansion of the expandable elements 62-66 as well as in carrying out a further procedure, such as an angioplasty procedure for opening a closed vessel. This can be carried out at the same time as deployment of the drug delivery device.

In practice, the drug delivery device is fed endoluminally through the vasculature of a patient, via a delivery sheath or catheter, up to the treatment site, at which point the expandable element or elements of the device are positioned beyond the extremity of the delivery catheter or sheath and thereafter expanded to the vessel wall. As will be apparent in particular from FIGS. 1-3, once the expandable elements of the drug delivery device have been radially expanded, the body portions 16, 36, 38 and 66-70 will come into abutment with the vessel wall to administer the drug into the vessel tissue by direct contact of the expandable elements and bioactive material. The expandable elements can remain in the expanded condition for an extended period of time by virtue of the fact that blood can continue to flow through the vessel, through the open braiding structure of the end cones. Once the drug administration has been completed, the expandable elements can be contracted radially, by extending the elements longitudinally as described above, whereupon the drug delivery device can be withdrawn from the patient, typically through a delivery catheter or sheath.

With respect to the embodiment of FIGS. 6 and 7, the device 110 can likewise be delivered endoluminally through a patient's vasculature through a sheath or catheter and in this particular instance the vessel opened by inflation of the balloons 112-116. Once the vessel has been forced open, the balloons can be deflated, whereupon they will remain within the volume of the expandable elements 62-66, the latter remaining in the expanded condition and therefore pressing their body portions against the vessel wall for delivery of the bioactive agent to the vessel tissue, all while allowing blood to flow through the vessel.

Although the embodiment of FIGS. 6 and 7 has three expandable elements 62-66 and an equivalent number of inflatable balloons, in other embodiments there may be a different number of expandable elements, for example a single expandable element as in the embodiment of FIG. 1, which would have a single inflation balloon therewithin, two expandable elements as in the embodiment of FIG. 2, in which case the device would have two inflatable balloons, or any other number of expandable elements and corresponding number of inflation balloons. Some embodiments may have some expandable elements which expand by manipulation of the catheter assembly 14 rather than by an associated balloon.

Figure 8:
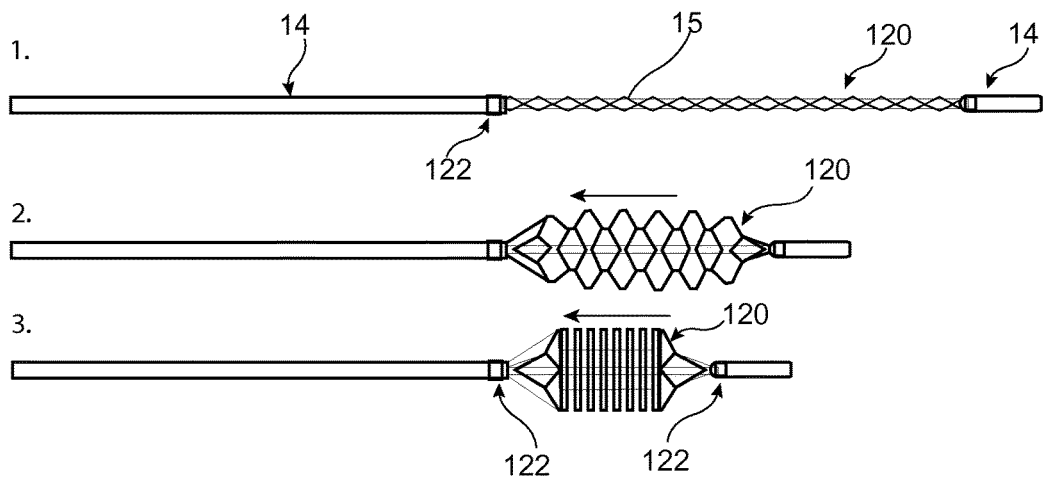
FIG. 8 is a series of schematic diagrams depicting another embodiment of endoluminal delivery device.

Referring now to FIG. 8, this shows another embodiment of endoluminal drug delivery device. The top sketch in FIG. 8 shows an embodiment of device having inner and outer catheter elements 14 and 15, as with the embodiments previously described, and with the outer catheter element 14 being in two parts having an expandable structure 120 therebetween. In this embodiment, the expandable structure 120 is, in place of being braided, a knitted structure formed from a wire of any of the types described above. With reference to the second sketch in FIG. 8, as the inner catheter 15 is retracted in the direction of the arrow in the second sketch, the knitted structure 120 will be compressed longitudinally, resulting in its radial expansion as shown in the sketch. Further retraction of the inner catheter 15, as shown in the third sketch of FIG. 8, will result in substantially complete longitudinal compression of the expandable element 120 and greatest radial expansion. This will be apparent from the second and third sketches of FIG. 8. The knitted structure preferably has a very open wire arrangement at the proximal and distal ends of the expandable element 120, in order to allow substantially unimpeded flow of blood through the vessel when the device is deployed.

Figure 9:
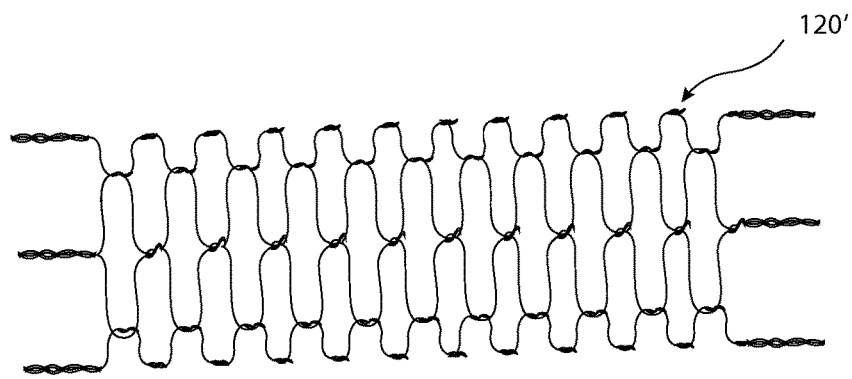
FIG. 9 is a schematic diagram of an embodiment of knitting pattern for the device of FIG. 8.

With reference to FIG. 9, this shows a first example of knitted wire structure for the expandable element 120 of FIG. 8. In the example of FIG. 9, the knitted structure is formed by one or more wires which are formed in undulating lengths, with the wires being wound around one another at their apices. Each wire provides a series of substantially horizontal (to the longitudinal direction of the device) wire sections generating a relatively large radial opening force when the structure is radially expanded as depicted in FIG. 9. At the ends of the knitted sections of the wires, the wires may be wrapped around themselves in the longitudinal direction, these forming the end sections of the expandable structure 120.

Figure 10:
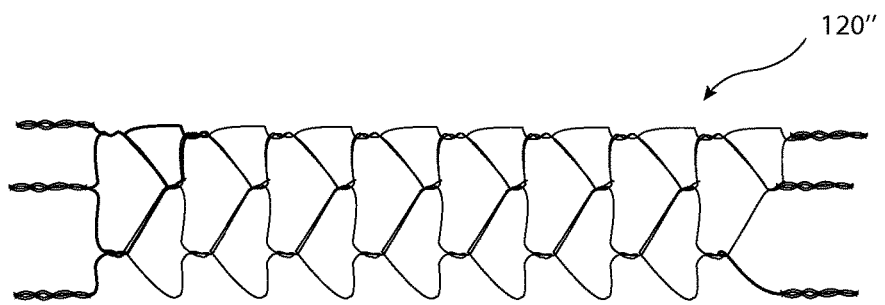
FIG. 10 is a schematic diagram of another embodiment of knitting pattern for the device of FIG. 8.

With reference to FIG. 10, this shows another example of knitted structure 120, in which each wire element could be described as having a sawtooth shape, with the wires being wrapped around one another at the apices of the sawtooth shape. Again, at the ends of the knitted structure, the wires are wrapped around one another in the longitudinal direction of the device, to form the open ends to the expandable structure.

A knitted structure can exert substantially greater opening force, which can assist in vessel dilatation and in some instances without the need for use of a dilation balloon.

In some instances, the use of a wire structure for the expandable frame element will result in the wires becoming partially embedded within the tunica intima of the vessel. This can be advantageous in some circumstances, particularly when it is desired to administer bioactive agents directly into the tunica intima, for instance during a dilatation procedure.

In the preferred embodiments, the expandable part of the drug delivery device is preferably made of a single braided or knitted structure, and in cases where the device has a plurality of expandable elements, these are created by means of constraining elements 50 which may be sleeves as disclosed above, a bonding agent or simply having a braided or knitted structure which is tighter at the points of constriction between adjacent expandable elements. Where bonding agent is used, this could be to a part of the delivery catheter 14.

In other embodiments, each expandable element may be made of its own individual braided or knitted structure, in which case the plurality of braided or knitted structures can be coupled to one another, for example by a constraining sleeve or other suitable mechanism.

It is not necessary for the expandable element to be made of a braided or knitted structure as in the above-described embodiments. The body portion of the expandable member could have other structures, for example a rolled sleeve or the like, in which case the end portions 18, 20 could be struts or the like attached to the expandable sleeve. A person skilled in the art will be able from the teachings herein to devise expandable structures having other components and structures.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A vascular delivery device for delivering a bioactive agent to a vessel wall, comprising:
   an expandable frame element having a body portion formed of at least one braided or knitted wire and first and second end portions formed of at least one braided or knitted wire, the body portion being radially expandable from a contracted to a deployed configuration, and having an open interior and an outer surface;
   the first and second end portions having an open structure allowing passage to the open interior of the body portion;

a catheter assembly on which the expandable frame is disposed, wherein the first and second end portions are connected to the catheter assembly;

and a bioactive material disposed at least on the outer surface of the body portion;

wherein the body portion has, in the expanded condition, a knit or braid weave which is tighter than the knit or braid weave of the first and second end portions wherein the catheter assembly includes first and second catheter elements, each attached to a respective one of the first and second end portions, the first and second catheter elements being movable towards and away from one another, said movement causing radial expansion and contraction of the body member, and wherein movement of the catheter elements towards one another causes longitudinal contraction of the expandable frame element and radial expansion of the body member, whereas movement of the catheter elements away from one another causes longitudinal expansion of the expandable frame element and radial contraction of the body member.

2. The vascular delivery device according to claim 1, wherein the body portion is generally hollow.

3. The vascular delivery device according to claim 1, wherein the body portion is generally cylindrical.

4. The vascular delivery device according to claim 1, wherein the first and second end portions have a tapering configuration in the deployed condition of the body portion and include a narrow end connected to the catheter assembly and a wide end connected to the body portion.

5. The vascular delivery device according to claim 4, wherein the first and second end portions have generally conical shapes when the body portion is in its deployed configuration.

6. The vascular delivery device according to claim 1, wherein the expandable frame element is self-supporting at least in the expanded configuration.

7. The vascular delivery device according to claim 1, wherein the first and second catheter elements are telescopic elements.

8. The vascular delivery device according to claim 1, comprising at least one expansion device disposed within the expandable frame element.

9. The vascular delivery device according to claim 8, wherein the at least one expansion device is an inflatable balloon.

10. The vascular delivery device according to claim 9, wherein the inflatable balloon is inflatable to expand the frame element and wherein the frame element remains in the expanded configuration on subsequent deflation of the balloon.

11. The vascular device according to claim 1, wherein the bioactive material is paclitaxel.

12. The vascular device according to claim 1, wherein the bioactive material is sirolimus.

13. The vascular device according to claim 1, wherein the body portion comprises a material selected from the group consisting of spring steel, a shape memory alloy and Nitinol.

14. A vascular delivery device for delivering a bioactive agent to a vessel wall, comprising:

a first and a second expandable frame element each having a body portion formed of at least one braided or knitted wire and first and second end portions formed of at least one braided or knitted wire, the body portion being radially expandable from a contracted to a deployed configuration, and having an open interior and an outer surface; the first and second end portions having an open structure allowing passage to the open interior of the body portion;

a catheter assembly on which the first and second expandable frame elements are disposed, wherein the first and second end portions of each of the first and second expandable frame elements connect to the catheter assembly, and wherein the first and second expandable frame elements are disposed adjacent to one another in a longitudinal direction of the device;

a sleeve positioned between the first and second expandable frame elements, wherein the sleeve is slidable over the first and second expandable frame elements on the catheter assembly;

and a bioactive material disposed at least on the outer surface of at least one of the body portions;

wherein the body portions have, in the expanded condition, a knit or braid weave which is tighter than the knit or braid weave of the first and second end portions.

15. The vascular device according to claim 14, wherein the bioactive material is paclitaxel.

16. The vascular device according to claim 14, wherein the bioactive material is sirolimus.

* * * * *

UNITED STATES PATENT AND TRADEMARK OFFICE
CERTIFICATE OF CORRECTION

PATENT NO. : 9,795,772 B2  
APPLICATION NO. : 14/724047  
DATED : October 24, 2017  
INVENTOR(S) : Aggerholm et al.

Page 1 of 1

It is certified that error appears in the above-identified patent and that said Letters Patent is hereby corrected as shown below:

On the Title Page

Item (72) should read:  
(72) Inventors: Steen Aggerholm, Heddinge (DK);  
                Sean D. Chambers, Bloomington, IN (US);  
                Paul Munk Hansen, Bjaeverskov (DK)

Signed and Sealed this  
Twenty-fourth Day of April, 2018

Andrei Iancu  
*Director of the United States Patent and Trademark Office*